(12) United States Patent
Libby (10) Patent No.: US 7,965,183 B1
(45) Date of Patent: *Jun. 21, 2011

(54) SYSTEMS AND METHODS FOR DETERMINING AUTHENTICITY OF SUBSTANCES

(75) Inventor: Vibeke Libby, Woodside, CA (US)

(73) Assignee: Northrop Grumman Space and Mission Systems Corporation, Los Angeles, CA (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/775,587

(22) Filed: Jul. 10, 2007

(51) Int. Cl.
*G08B 1/08* (2006.01)

(52) U.S. Cl. .............. 340/539.22; 340/539.1; 340/10.1

(58) Field of Classification Search .......... 340/511, 340/506, 539.22, 545.4; 250/281–300, 316.1, 250/317.1, 318, 319
See application file for complete search history.

(56) References Cited

U.S. PATENT DOCUMENTS

| | | | |
|---|---|---|---|
| 6,610,977 B2 * | 8/2003 | Megerle | 250/287 |
| 7,180,418 B1 * | 2/2007 | Willms et al. | 340/568.1 |
| 7,403,113 B2 * | 7/2008 | Moon et al. | 340/539.22 |
| 7,411,489 B1 * | 8/2008 | Elwell et al. | 340/501 |
| 7,436,991 B2 * | 10/2008 | Greenbaum et al. | 382/128 |
| 7,486,193 B2 * | 2/2009 | Elwell | 340/573.1 |
| 2005/0037776 A1 | 2/2005 | Perez-Breva et al. | |
| 2009/0112101 A1 * | 4/2009 | Furness et al. | 600/477 |

* cited by examiner

*Primary Examiner* — Benjamin C Lee
*Assistant Examiner* — Peter C Mehravari
(74) *Attorney, Agent, or Firm* — Tarolli, Sundheim, Covell & Tummino LLP (57) ABSTRACT

One embodiment of the present invention includes a system for determining authenticity of substances. The system comprises a plurality of RF sensors distributed in a predefined location pattern relative to a location for placing a substance under analysis. Each of the RF sensors is configured to transmit a response to an interrogation signal with a unique identifier. The system also comprises an RF transmitter that transmits sequences of interrogation signals over different frequency bands at one or more power levels and an RF receiver that receives responses to the sequences of interrogation signals transmitted from the RF sensors. The system further comprises a response pattern analyzer that determines response patterns for the RF sensors to the interrogation sequences and transmits a difference indicator if at least one of the determined response patterns varies from as predetermined signature of an authentic substance.

23 Claims, 5 Drawing Sheets

SYSTEMS AND METHODS FOR DETERMINING AUTHENTICITY OF SUBSTANCES

TECHNICAL FIELD

The present invention relates generally to detections systems, and more particularly to systems and methods for determining authenticity of substances.

BACKGROUND

The development of security systems is becoming more of an important issue with regard to the safety and security of people. As an example, with the increased need for security in large public venues such as airports and stadiums, the implementation of security systems is becoming more prevalent. A number of security systems exist for the detection of contraband on a person, such as walk-through metal detectors and wands. However, such systems are typically limited in that they are capable only of detecting metal, and often only certain types of metals. Furthermore, it is not necessarily just people that need to be monitored for security purposes, but also the personal belongings of people. For example, people often bring carry-on items onto an airplane when they fly. While it is important to screen such carry-on items, such screening must be weighed against a competing concern with efficiency of security monitoring and the impingement of personal freedoms.

There are a variety of security measures in place to screen personal items. Some of them are large, complicated, and expensive, such as conveyor-belt fed X-ray machines that are typically employed in airports. Some measures are very simple, such as security personnel searching personal bags upon entering stadiums and festivals. However, all such systems can be easily spoofed by hiding contraband items in locations that appear to be obvious as something else, particularly in light of efficient security monitoring. For example, security personnel are unlikely to search what appears to be a typical twenty-ounce plastic bottle of soda because it would be inefficient and because people would be unhappy to have their drink poured out. However, a clever criminal could have hidden drugs, ammunition, or explosives in a recess behind the label, with real soda above and below the recess so as to make it look like a full bottle of soda. As another example, the bottle may appear to contain soda, whereas the liquid inside may not actually be soda, or may be soda that includes alcohol, such that it is smuggled into an area where alcohol is prohibited. Therefore, existing security screening measures may be insufficient to provide adequate public safety.

SUMMARY

One embodiment of the present invention includes a system for determining authenticity of substances. The system comprises a plurality of RF sensors distributed in a predefined location pattern relative to a location for placing a substance under analysis. Each of the RF sensors is configured to transmit a response to an interrogation signal with a unique identifier. The system also comprises an RF transmitter that transmits sequences of interrogation signals over different frequency bands at one or more power levels and an RF receiver that receives responses to the sequences of interrogation signals transmitted from the RF sensors. The system further comprises a response pattern analyzer that determines response patterns for the RF sensors to the interrogation sequences and transmits a difference indicator if at least one of the determined response patterns varies from a predetermined signature of an authentic substance.

Another embodiment of the present invention includes a system for determining authenticity of substances. The system comprises a plurality of means for responding to an interrogation signal with a wireless unique identifier. The plurality of means for responding is arranged in a predefined location pattern relative to a location for placing the substance under analysis. The system also comprises means for transmitting sequences of interrogation signals at a plurality of power levels and means for receiving the wireless unique identifier of the plurality of means for responding for the sequences of the interrogation signals. The system also comprises means for housing the plurality of means for responding such that a given wireless unique identifier does not interfere with another wireless unique identifier. The system also comprises means for determining response patterns for the plurality of RF sensors to the interrogation sequences. The system further comprises means for determining if response patterns vary outside a predetermined signature of an authentic substance, and means for providing an indication if the response patterns vary outside the predetermined signature of an authentic substance.

Another embodiment of the present invention includes a method for determining authenticity of a substance. The method comprises transmitting sequences of interrogation signals in proximity of a known authentic substance over a plurality of different frequency bands at one or more power levels to a plurality of RF sensors distributed in a predefined location pattern. Each RF sensor is configured to respond to an interrogation signal with a unique identifier. The method also includes registering a plurality of response pattern signatures for the known authentic substance based on first response patterns of the plurality of RF sensors to the sequence of interrogation signals. The method also includes transmitting the sequences of interrogation signals in proximity of a substance under analysis that is purported to be the same as the known authentic substance over the plurality of different frequency bands at the one or more power levels to the plurality of RF sensors. The method also includes analyzing second response patterns for each of the plurality of RF sensors to the sequence of interrogation signals. The second response patterns are associated with the substance under analysis. The method further includes transmitting a difference indicator if at least one of the second response patterns varies from a predetermined threshold associated with the plurality of registered response pattern signatures.

DETAILED DESCRIPTION

The present invention relates to systems and methods for determining authenticity of substances. The systems and methods employ radio frequency (RF) sensor responses to interrogation signals of an RF transmitter to determine response patterns associated with a plurality of RF sensors that are arranged in a predefined location pattern relative to a substance to be analyzed. The response patterns can be compared with registered response pattern signatures associated with a corresponding known authentic substance. Even slight changes in these response patterns can signify a difference between the substance under analysis and the known authentic substance. The RF transmitter can be configured to hop between a plurality of frequency bands and a plurality of different power levels in obtaining the response patterns of both the known authentic substance and the substance under analysis. As such, upon the RF sensor responses being received by an RF receiver, a response pattern analyzer can ascertain differences in the frequency bands and the power levels of the responses for a given series of interrogation signals to determine if the substance under analysis is authentic.

The present invention can employ RF commercial off the shelf (COTS) technology, and therefore can be implemented at relatively low costs. Each RF sensor is in a unique position in space with respect to the transmitter and the substance under analysis, and can thus provide unique responses to the series of interrogation signals. The RF sensors can be arranged in the predefined location pattern within a semi-enclosed housing, such that the responses to the series of interrogation signals do not interfere with each other. Thus, the responses for a known authentic substance can be very accurate, such that the response pattern signature for the known authentic substance can include a set of response tolerances that is substantially precise. As a result, when comparing responses for a substance under analysis, slight deviation from the response tolerances for a given frequency band and/or a given power level can result in an indicated difference between the substance under analysis and the known authentic substance.

The present invention can be employed in any of a variety of different applications. For example, the present invention can be employed as part of a security system, such as at an airport or in a large public venue (e.g., stadium or festival). Thus, pre-approved categories of substances can be analyzed to determine their authenticity to prevent the smuggling of drugs, alcohol, explosives, and/or weapons into the prohibitive public setting. As another example, the present invention can be used for quality control in the food and beverage industry, such that a given item of food or beverage can be analyzed to determine purity or quality. As yet another example, the present invention can be implemented in an anti-counterfeiting role, such that money, precious coins, and/ or rare materials can be analyzed to determine if they are authentic or if they are counterfeit. As such, the present invention can be implemented in any of a variety of ways.

Figure 1:
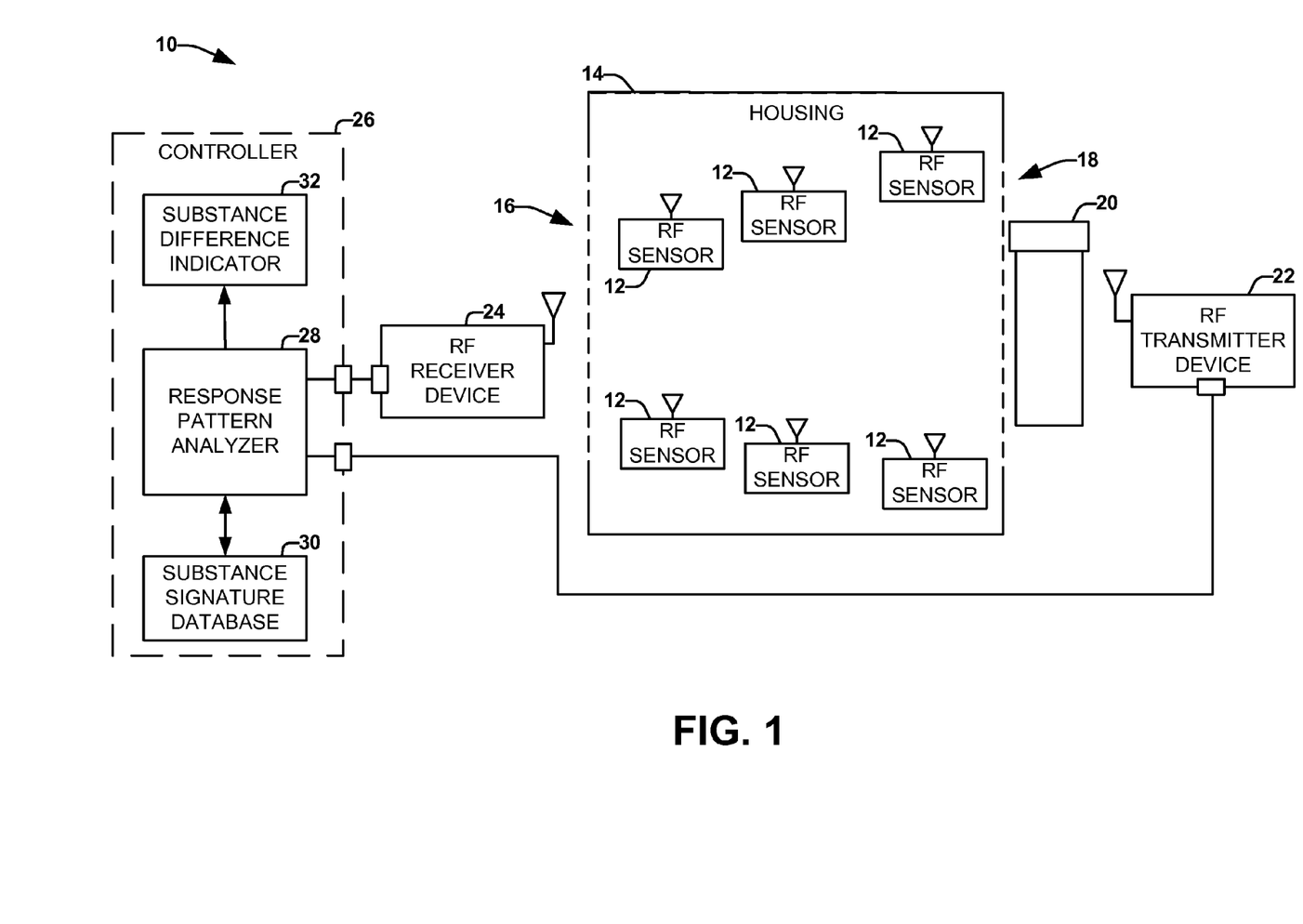
FIG. 1 illustrates an example of a diagram of a system for determining authenticity of substances in accordance with an aspect of the present invention.

FIG. 1 illustrates an example of a system 10 for determining authenticity of substances in accordance with an aspect of the present invention. The system 10 can be implemented in any of a variety of environments, such as an airport security checkpoint. The system 10 includes a plurality of radio frequency (RF) sensors 12 that can be arranged in a predefined location pattern. In the example of FIG. 1, the RF sensors 12 are demonstrated as being mounted within a housing 14. The housing 14 can be semi-enclosed, such that dashed lines 16 and 18 each represent openings of the housing 14. As an example, the housing 14 can be a substantially conical aluminum housing with the openings 16 and 18 being located at each of opposite ends of the housing 14. Also in the example of FIG. 1, a substance under analysis 20 is demonstrated at the opening 18 just outside the housing 14. As described herein, the substance under analysis 20 can be any of a variety of substances and/or materials for which authenticity is in question. Thus, the system 10 is configured to determine the authenticity of the substance under analysis 20.

The system 10 includes an RF transmitter device 22 and an RF receiver device 24 that are each coupled to a controller 26. The RF transmitter device 22 is configured to transmit sequences of interrogation signals through the substance under analysis 20 and through the housing 14. The RF transmitter device 22 can transmit the interrogation signals over a set of frequency bands at one or more power levels for each given interrogation sequence. As an example, the RF transmitter device 22 transmits the interrogation signals employing spread-spectrum frequency hopping that generates pseudo-random frequency bands over different interrogation sequences. A given interrogation sequence can include, for example, 50 interrogation signals at different frequency bands at a given power level, and can repeat the generation of 50 interrogation signals at each of a plurality of different power levels.

The interrogation signals are received by each of the RF sensors 12, such that each of the RF sensors 12 is configured to generate a signal in response to the interrogation signal. The response signal from each of the RF sensors 12 can incorporate an identifier that is unique to the specific RF sensor 12. The RF receiver device 24 receives the response signals that are transmitted from each of the plurality of RF sensors 12. The RF receiver device 24 provides the response signals received from the RF sensors 12 to the controller 26.

The controller 26 includes a response pattern analyzer 28 that is configured to provide commands to the RF transmitter device 22 and receive the response signals from the RF receiver device 24. For example, the response pattern analyzer 28 can be configured to step through the sequences of interrogation signals, such that the response pattern analyzer 28 initiates the RF transmitter device 22 to generate each sentience of the interrogation signals for a given frequency and power level. Thus, the response pattern analyzer 28 can be set to expect responses that correspond to the sequence of the interrogation signals that is transmitted by the RF transmitter device 22. Upon receiving the response signals, the response pattern analyzer 28 determines response patterns for each of the RF sensors 12 and compares the response patterns of the associated RF sensors 12 to one or more predetermined expected response thresholds. Each of the RF sensors 12 can have its own unique set of threshold values.

At certain power levels and frequency hands, a given RF sensor 12 may not respond, or may not respond with enough power for the RF receiver device 24 to have a valid read for that respective RF sensor 12. Additionally, the RF receiver device 24 may receive a response signal from a given one of the RF sensors 12 that deviates from the expected response thresholds. These failures and/or deviations may be due to the chemical and/or material composition of the substance under analysis 20. The combination of valid reads and failed or invalid reads over an interrogation sequence provide a response pattern for a given RF sensor 12. The response pattern can be represented as a binary sequence with valid reads being represented with a logic "1" and invalid reads being represented as a logic "0" for each power level interrogation sequence integrate over all frequency bands. Thus, a difference in the binary sequence between a sequence of interrogation signals for the substance under analysis 20 and the expected response thresholds can indicate a difference between the substance under analysis 20 and a known authentic substance from which the expected response thresholds were generated.

For example, the predetermined expected response thresholds can be determined by initiating a plurality of sequences of interrogation signals for a known authentic substance that corresponds to the substance under analysis 20. It is to be understood that, as described herein, the known authentic substance is a substance that is known to be authentic, such that the known authentic substance can be registered as a calibration agent for the substance under analysis 20. As an example, the system 10 can register the known authentic substance by performing the sequences of interrogation signals on the known authentic substance to generate a plurality of response pattern signatures that correspond to the predetermined expected response thresholds. The response pattern signatures for the known authentic substance are stored by the response pattern analyzer 28 in a substance signature database 30 during a registration process. The system 10 can thus register any number of any of a variety of substances and store the respective response pattern signatures in the substance signature database 30.

Upon analyzing the substance under analysis 20, an operator of the system 10, automated or otherwise, can indicate to the controller 26 if the substance under analysis 20 is what it is purported to be. The response pattern analyzer 28 can thus access the response pattern signatures for the purported substance from the substance signature database 30, such that the response patterns for the substance under analysis 20 can be compared with the response pattern signatures. As an example, in an airport security environment, upon security personnel seeing a label on a bottle of cola, the brand of cola can be entered into the controller by the security personnel. Therefore, the security personnel can implement the system 10 to determine if the liquid in the bottle of cola is actually the cola that it is purported to be, or is not contaminated with any additional chemicals and/or materials.

Upon accessing the response pattern signatures from the substance signature database 30, the system 10 can begin obtaining the response patterns for the substance under analysis 20. If the response patterns for the substance under analysis 20 are substantially the same as the response pattern signatures, or sufficiently within predetermined difference thresholds associated with the response pattern signatures, then the substance under analysis 20 is authentic. However, if there are one or more differences between the response patterns for the substance under analysis 20 and the response pattern signatures, or one or more of the response patterns are outside of the predetermined difference thresholds associated with the response pattern signatures, then the substance under analysis 20 is not authentic. The response pattern analyzer 28 thus provides a difference indicator signal to a substance difference indicator 32 to indicate to an operator of the system 10 that the substance under analysis 20 is not authentic. The substance difference indicator 32 can be any of a variety of indications, such as a flashing light, a message on a computer screen, and/or an audible indication.

Figure 2:
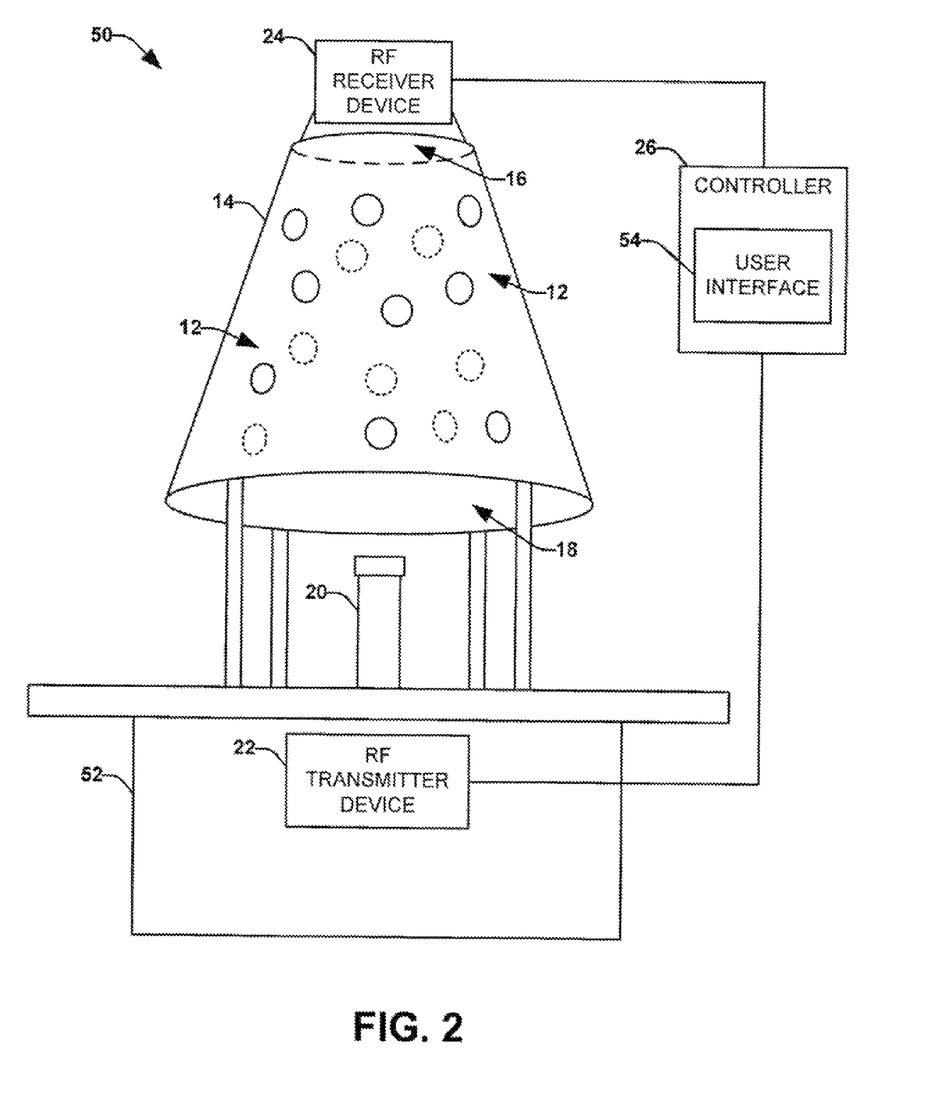
FIG. 2 illustrates an example of a system for determining authenticity of substances in accordance with an aspect of the present invention.

FIG. 2 illustrates an example of a system 50 for determining authenticity of substances in accordance with an aspect of the present invention. The system 50 can be substantially similar to the system 10 in the block diagram example of FIG. 1. Therefore, like reference numbers are to be used and reference is to be made to the example of FIG. 1 in the discussion of FIG. 2.

The RF sensors 12 are demonstrated in the example of FIG. 2 as being arranged in a predefined location pattern within the semi-enclosed housing 14. In the example of FIG. 2, the housing 14 is demonstrated as substantially conical, with the small opening 16 at the top of the housing 14 and the large opening 18 at the bottom of the housing 14. It is to be understood that the RF sensors 12 that are demonstrated with dashed lines are intended to represent those that are configured on the insides of the far surface of the housing 14. Therefore, the predefined location of the RF sensors 12 can encompass the entire circumferential surface of the inside of the housing 14.

The system 50 includes the RF transmitter device 22 configured in a base structure 52. The RF transmitter device 22 can thus be configured to transmit the sequences of interrogation signals upward through the substance under analysis 20 and into the housing 14 to be received by the RF sensors 12. The RF receiver device 24 is located at the top of the housing 14 at the small opening 16. In the example of FIG. 2, the housing 14 can have a shape and determinative dimensions that are functional with regard to the RF sensor responses transmitted to the RF receiver device 24 in response to the interrogation signals transmitted from the RF transmitter device 22. Specifically, the substantially conical shape of the housing 14 can be such that the RF sensor responses do not interfere with each other, as received by the RF receiver device 24. Therefore, the RF sensor responses can more accurately indicate very slight differences between response patterns of the substance under analysis 20 and the response pattern signatures of the known authentic substance. It is to be understood that the example of FIG. 2 is not limited to a substantially conical shape of the housing 14, but that any of a variety of shapes and dimensions can be implemented to provide for non-interference of the RF sensor responses from the RF sensors 12 to the RF receiver device 24.

In the example of FIG. 2, the controller 26 is demonstrated as coupled to both the RF transmitter device 22 and the RF receiver device 24. As described in the example of FIG. 1, the controller 26 can include the response pattern analyzer 28, the substance signature database 30, and the substance difference indicator 32. In addition, in the example of FIG. 2, the controller 26 includes a user interface 54. The user interlace 54 can be configured to allow a user of the system 50 to interact with the controller 26, such as to enter a substance that the substance under analysis 20 purports to be, or to allow the user to receive visual and/or audible indications of the authenticity of the substance under analysis 20. The user interface 54 can be any of a variety of interfaces, such as a touchscreen, a keyboard and monitor, etc.

Although the controller 26 is demonstrated in the example of FIG. 2 as external to the base structure and the RF transmitter device 22 and RF receiver device 24, it is to he understood that all of or portions of all of the controller 26 can be configured internal to one or more of the base structure 52, the RF transmitter device 22, and the RF receiver device 24. Therefore, one or more of the components of the controller 26 can be configured separate from the system 50. As an example, the system 50 can interact with a separate computer system (not shown) that includes one or more of the response pattern analyzer 28, the substance signature database 30, the substance difference indicator 32, and the user interface 54. As another example, the separate computer system can interact with a plurality of systems 50 concurrently, such that one or more of the components of the controller 26 can be shared amongst the separate plurality of systems 50.

The RF transmitter device 22, the RF receiver device 24, and the RF sensors 12 can be implemented as RF commercial off the shelf (COTS) technology, and therefore can be small and can be implemented at relatively low costs. As a result, the system 50 can be configured as a portable or semi-portable substance analysis device. As an example, the base structure 52 can include wheels, or the system 50 can be configured as a collapsible system, such that it can be easily disassembled and carried to and from separate locations. For example, the RF and electronic components of the system 50 can be battery operated, such that the system 50 can interface with a laptop computer and be field operated. As an example, the system 50 can be implemented to analyze water samples in an environment where electricity is not readily available. Alternatively, the system 50 or portions of the system 50, such as the base structure 52, can be fixed, such that the base structure 52 can incorporate a conveyor system to rapidly feed substances under analysis 20 through the system 50, such as in an airport security setting. Therefore, the system 50 can be implemented in any of a variety of ways.

Figure 3:
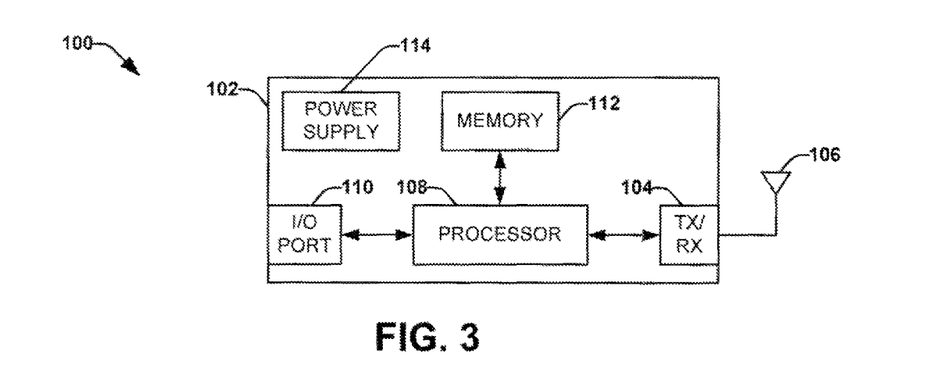
FIG. 3 illustrates an example of a diagram of an RF transmitter/receiver device in accordance with an aspect of the present invention.

FIG. 3 illustrates an example of a diagram of an RF transmitter/receiver device 100 in accordance with an aspect of the present invention. The RF transmitter/receiver device 100 can be substantially similar to the RF transmitter device 22 and/or the RF receiver device 24 in the block diagram example of FIGS. 1 and 2. Specifically, the RF transmitter/receiver device 100 can be a COTS RF component, such that it can be implemented and programmed to function as either the RF transmitter device 22 or the RF receiver device 24. Therefore, like reference numbers are to be used and reference is to be made to the example of FIGS. 1 and 2 in the discussion of FIG. 3. However, it is to be understood that the systems 10 and 50 in the examples of FIGS. 1 and 2, respectively, are not intended to be limited to the same type of device for use as both the RF transmitter 22 and RF receiver 24, but that separate types of devices (e.g., manufacturers and/or brands) can likewise be implemented for both the RF transmitter 22 and RF receiver 24.

The RF transmitter/receiver device 100 is contained within a housing 102 and includes an RF transceiver 104. In the implementation of the RF transmitter/receiver device 100 as the RF transmitter device 22, the RF transceiver 104 can be operable to broadcast the sequences of the interrogation signals to the RF sensors 12 via an antenna 106. The RF transceiver 104 can also be operable to receive RF responses from one or more of the RF sensors 12. A processor 108 can be configured to frequency hop through a plurality of frequency bands and can be programmed to exercise a plurality of different power levels to establish the sequences of interrogation signals. As an example, the processor 108 can issue commands received from the controller 26 via an input/output (I/O) port 110 that correspond to a sequence of the transmission frequencies and/or power levels for the interrogation signals.

In the implementation of the RF transmitter/receiver device 100 as the RF receiver device 24, the RF transceiver 104 can be operable to receive RF responses from one or more of the RF sensors 12 via the antenna 106. The processor 108 can be configured to determine and/or transmit responses for a given interrogation sequence for each of the RF sensors 12 to the I/O port 110 for processing by an external device. As an example, the received transmissions can be provided to the controller 26 via the I/O port 110, such that the controller 26 can track a number of the RF responses relative to the number of interrogation signals.

The antenna 106 can be configured internal or external to the housing 102. The RF transmitter/receiver device 100 can include a memory 112. The memory 112 can be internal or external to the processor 108, and can be implemented for any of a variety of functions, such as to implement some of the features that can be performed by the controller 26. The memory 112 can be preprogrammed, or can be programmed via the I/O port 110. The RF transmitter/receiver device 100 can also include a power supply 114 to provide operating power. The power supply 114 can be a battery or a power supply powered by, for example, a standard wall plug.

Figure 4:
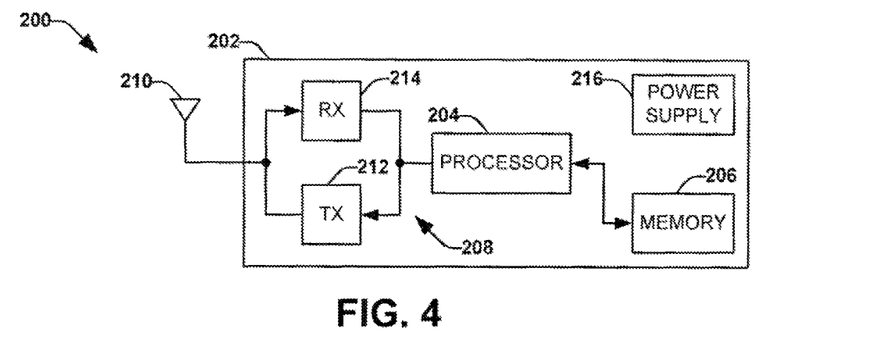
FIG. 4 illustrates an example of a diagram of an RF sensor in accordance with an aspect of the present invention.

FIG. 4 illustrates an example of a diagram of an RF sensor 200 in accordance with an aspect of the present invention. The RF sensor 200 can be substantially similar to any of the RF sensors 12 in the block diagram example of FIGS. 1 and 2. Therefore, like reference numbers are to be used and reference is to be made to the example of FIGS. 1 and 2 in the discussion of FIG. 4.

The RF sensor 200 is maintained within as housing 202, and includes a processor 204 or controller which can be programmed to respond to an interrogation signal of the RF transmitter device 22 with a unique identifier associated with the RF sensor 200. The RF sensor 200 can be configured as active or passive. As an example, an active sensor emits signals at regular preset intervals, while a passive sensor is powered by a received interrogation signal. A memory 206 is included in the RF sensor 200 for storing, among other things, program code executed by the processor 204. The memory 206 can also serve as a storage medium for storing a unique identification code used to designate and distinguish the RF sensor 200 from the other RF sensors 12 within the housing 14. The memory 206 can be external or internal to the processor 204. The RF sensor 200 includes an RF section 208 interconnected between the processor 204 and an antenna 210 that can be configured external or internal to the housing 202. The RF section 208 includes an RF receiver 212 which receives the RF interrogation signals from the RF transmitter device 22 via the antenna 210. The RF section 208 also includes an RF transmitter 214 operable to transmit RF response signals to the RF receiver device 24 that include the unique identifier via the antenna 210. A power supply 216 may be included, such as in an active RF sensor configuration, to provide operating power to the RF sensor 200.

Figure 5:
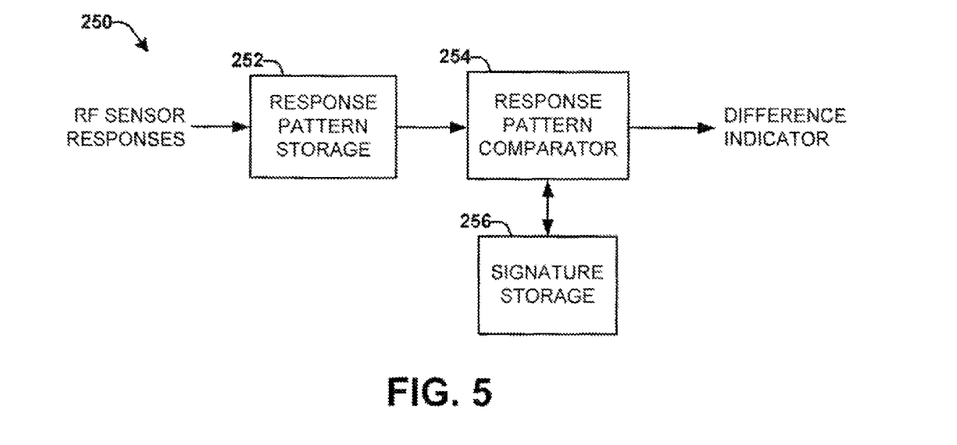
FIG. 5 illustrates an example of a diagram of a response pattern analyzer in accordance with an aspect of the present invention.

FIG. 5 illustrates a block diagram of a response pattern analyzer 250 in accordance with an aspect of the present invention. The response pattern analyzer 250 can be substantially similar to the response pattern analyzer 28 in the block diagram example of FIG. 1. Therefore, like reference numbers are to be used and reference is to be made to the example of FIG. 1 in the discussion of FIG. 5.

The response pattern analyzer 250 is configured to receive a plurality of RF sensor responses from the plurality of RF sensors 12 over one or more sequences of interrogation signals of the substance under analysis 20, and to store the RF sensor response patterns associated with each RF sensor for a given sequence of interrogation signals in an RF sensor response pattern storage 252. The response pattern analyzer 250 includes an RF sensor pattern comparator 254 that compares the stored sensor response patterns in the RF sensor response pattern storage 252 with a plurality of response pattern signatures in a response pattern signature storage 256.

The response pattern signatures can be pre-stored based on registering response patterns for a known authentic substance that corresponds to what the substance under analysis is purported to be. As an example, the response pattern signature storage 256 can be loaded with the response pattern signatures from the substance signature database 30 based on input from a user or through an automated loading process. In addition, the response pattern signatures can include difference thresholds that define a range of acceptable tolerances for the response patterns of the substance under analysis 20. The RF sensor response pattern comparator 254 is configured to transmit a difference indicator signal, such as to the substance difference indicator 32, in response to a determination that one or more of the response patterns of the substance under analysis 20 deviate from the response pattern signatures in the response pattern signature storage 256. As an example, one or more of the response patterns may be outside the range of acceptable tolerances of the difference thresholds defined in the response pattern signature storage 256. As a result, the difference indicator can provide indication to an operator or to a user interface, such as the user interface 54 in the example of FIG. 2, that the substance under analysis 20 is not authentic.

Figure 6:
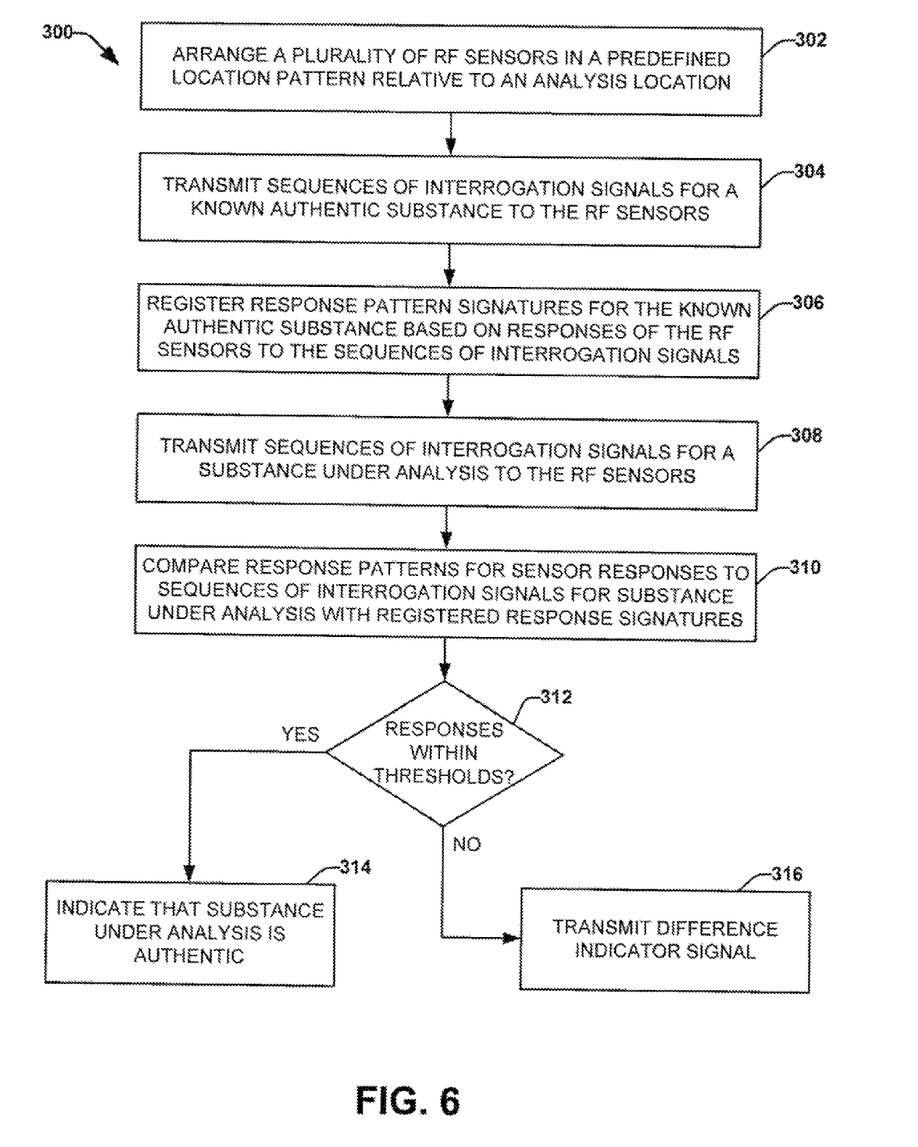
FIG. 6 illustrates an example of a method for determining authenticity of substances in accordance with an aspect of the present invention.

In view of the foregoing structural and functional features described above, a method will be better appreciated with reference to FIG. 6. It is to be understood and appreciated that the illustrated actions, in other embodiments, may occur in different orders and/or concurrently with other actions. Moreover, not all illustrated features may be required to implement a method. It is to be further understood that the following methodologies can be implemented in hardware (e.g., a computer or a computer network as one or more integrated circuits or circuit boards containing one or more microprocessors), software (e.g., as executable instructions running on one or more processors of a computer system), or any combination thereof.

FIG. 6 illustrates an example of a method 300 for determining authenticity of substances in accordance with an aspect of the present invention. The methodology begins at 302, in which a plurality of RF sensors are arranged in a predefined location pattern relative to an analysis location. The plurality of RF sensors can be COTS components that each have a unique RF identifier, and the predefined location pattern can be within a semi-enclosed housing that allows each of the RF sensors to transmit its unique RF identifier in a manner that does not interfere with the other RF sensors. At 304, sequences of interrogation signals are transmitted for a known authentic substance to the RF sensors. The sequences of interrogation signals can incorporate transmissions at different frequency bands and at different power levels.

At 306, a plurality of response pattern signatures are registered for the known authentic substance based on the responses of the RF sensors to the sequences of interrogation signals. The response pattern signatures can include predefined difference thresholds that define an acceptable range of tolerances of response patterns. At 308, sequences of interrogation signals are transmitted for a substance under analysis to the RF sensors. The substance under analysis can be an unknown substance for which the authenticity is in question, and can be purported to correspond to the known authentic substance. The sequences of interrogation signals can be the same sequences as those that were transmitted to the known authentic substance, such that they can incorporate transmissions at different frequency bands and at different power levels.

At 310, the response patterns for the RF sensor responses to the sequences of interrogation signals for the substance under analysis are compared with the registered response pattern signatures. At 312, the method determines if the response patterns are within the difference thresholds defined by the registered response pattern signatures. If YES, that the response patterns are within the difference thresholds defined by the registered response pattern signatures, the method proceeds to 314. At 314, the substance under analysis is indicated as authentic, such that it is what it purports to be (i.e., corresponds to the known authentic substance). If NO, that the response patterns are not within the difference thresholds defined by the registered response pattern signatures, then the method proceeds to 316. At 316, a difference indicator signal is transmitted, such that the substance under analysis is not authentic.

Figure 7:
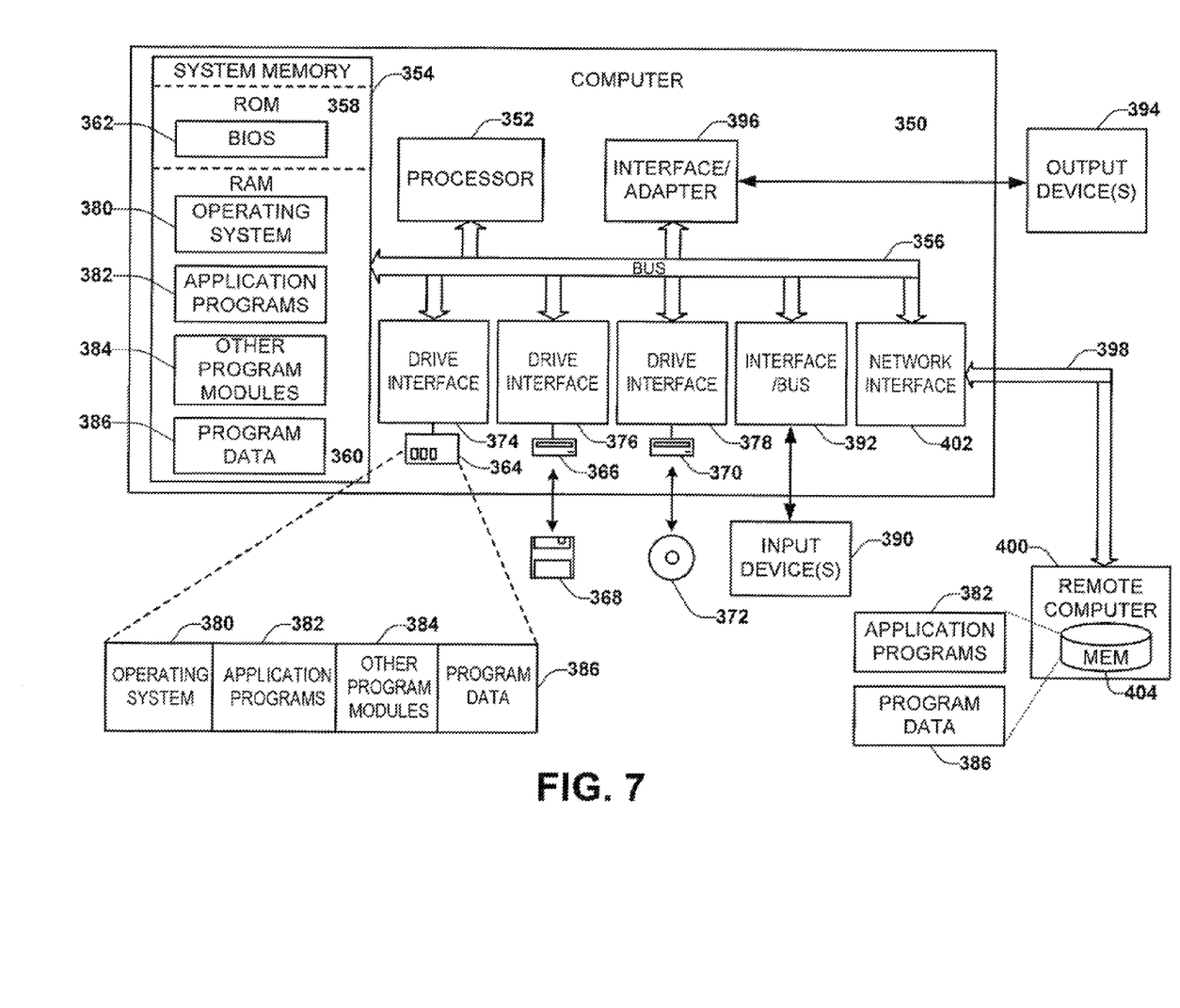
FIG. 7 illustrates an embodiment of a computer system that can be configured to implement a system for determining authenticity of substances in accordance with an aspect of the invention.

FIG. 7 illustrates a computer system 350 that can be employed to implement at least portions of the systems and methods described herein, such as based on computer executable instructions running on the computer system. The computer system 350 can be implemented on one or more general purpose networked computer systems, embedded computer systems, routers, switches, server devices, client devices, various intermediate devices/nodes and/or stand alone computer systems. Additionally, the computer system 350 can be implemented as part of the computer-aided engineering (CAE) tool running computer executable instructions to perform a method as described herein.

The computer system 350 includes a processor 352 and a system memory 354. A system bus 356 couples various system components, including the system memory 354 to the processor 352. Dual microprocessors and other multi-processor architectures can also be utilized as the processor 352. The system bus 356 can be implemented as any of several types of bus structures, including a memory bus or memory controller, a peripheral bus, and a local bus using any of as variety of bus architectures. The system memory 354 includes read only memory (ROM) 358 and random access memory (RAM) 360. A basic input/output system (BIOS) 362 can reside in the ROM 358, generally containing the basic routines that help to transfer information between elements within the computer system 350, such as a reset or power-up.

The computer system 350 can include a hard disk drive 364, a magnetic disk drive 366, e.g., to read from or write to a removable disk 368, and an optical disk drive 370, e.g., for reading a CD-ROM or DVD disk 372 or to read from or write to other optical media. The hard disk drive 364, magnetic disk drive 366, and optical disk drive 370 are connected to the system bus 356 by a hard disk drive interface 374, a magnetic disk drive interface 376, and an optical drive interface 378, respectively. The drives and their associated computer-readable media provide nonvolatile storage of data, data structures, and computer-executable instructions for the computer system 350. Although the description of computer-readable media above refers to a hard disk, a removable magnetic disk and a CD, other types of media which are readable by a computer, may also be used. For example, computer executable instructions for implementing systems and methods described herein may also be stored in magnetic cassettes, flash memory cards, digital video disks and the like.

A number of program modules may also be stored in one or more of the drives as well as in the RAM 360, including an operating system 380, one or more application programs 382, other program modules 384, and program data 386. The one or more application programs can include the systems and methods for determining authenticity of substances as previously described in FIGS. 1-6.

A user may enter commands and information into the computer system 350 through user input device 390, such as a keyboard, a pointing device (e.g., a mouse). Other input devices may include a microphone, a joystick, a game pad, a scanner, a touch screen, or the like. These and other input devices are often connected to the processor 352 through a corresponding interface or bus 392 that is coupled to the system bus 356. Such input devices can alternatively be connected to the system has 356 by other interfaces, such as a parallel port, a serial port or a universal serial bus (USB). One or more output device(s) 394, such as a visual display device or printer, can also be connected to the system bus 356 via an interface or adapter 396.

The computer system 350 may operate in a networked environment using logical connections 398 to one or more remote computers 400. The remote computer 400 may be a workstation, a computer system, a router, a peer device or other common network node, and typically includes many or all of the elements described relative to the computer system 350. The logical connections 398 can include a local area network (LAN) and a wide area network (WAN).

When used in a LAN networking environment, the computer system 350 can be connected to a local network through a network interface 402. When used in a WAN networking environment, the computer system 350 can include a modem (not shown), or can be connected to a communications server via a LAN. In a networked environment, application programs 382 and program data 386 depicted relative to the computer system 350, or portions thereof, may be stored in memory 404 of the remote computer 400.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for determining authenticity of substances, the system comprising:
    a plurality of radio frequency (RF) sensors distributed in a predefined location pattern relative to a location for placing a substance under analysis, each of the plurality of RF sensors being configured to transmit a response to an interrogation signal with a unique identifier;
    an RF transmitter that transmits a plurality of sequences of interrogation signals over a plurality of different frequency bands at one or more power levels;
    an RF receiver that receives responses to the plurality of sequences of interrogation signals transmitted from the plurality of RF sensors; and
    a response pattern analyzer that determines response patterns for the plurality of RF sensors to the interrogation sequences and transmits a difference indicator if at least one of the determined response patterns varies from a predetermined signature of an authentic substance.

2. The system of claim 1, wherein the RF interrogator transmits sequences of interrogation signals employing spread-spectrum frequency-hopping to generate pseudo-random frequency bands over different sequences of interrogation signals.

3. The system of claim 1, wherein the predetermined signature of the authentic substance comprises a plurality of registered response pattern signatures associated with a known authentic substance corresponding to the substance under analysis, the response pattern analyzer transmitting a difference indicator if the determined response patterns vary outside predetermined thresholds of the plurality of registered response pattern signatures.

4. The system of claim 1, wherein the predetermined signature of the authentic substance comprises a plurality of predetermined difference thresholds determined based on response patterns received upon obtaining a plurality of registered response pattern signatures associated with a known authentic substance corresponding to the substance under analysis.

5. The system of claim 1, further comprising a substance signature database configured to store a plurality of predetermined signatures of each of a plurality of known authentic substances, the plurality of predetermined signatures including a set of acceptable tolerances associated with each of the plurality of predetermined signatures.

6. The system of claim 1, wherein each of the response patterns is a binary sequence based on valid reads and failed reads for one or more of the sequences of interrogation signals at the one or more power levels.

7. The system of claim 1, wherein the response pattern analyzer comprises:
    an RF sensor response pattern storage for storing RF sensor response patterns from the RF receiver; and
    a RF sensor response pattern comparator that compares the stored RF sensor response patterns with the predetermined signature of the authentic substance.

8. The system of claim 1, further comprising a semi-enclosed metallic housing within which the plurality of RF sensors are distributed in the predefined location pattern.

9. The system of claim 8, wherein the housing is substantially conical in shape, and wherein the housing comprises a first opening at a wide end proximal to the location for placing the substance under analysis and a second opening at a narrow end distal from the location for placing the substance under analysis.

10. The system of claim 9, wherein the RF transmitter is located proximal to one of the first and second openings, and wherein the RF receiver is located proximal to the other of the first and second openings.

11. The system of claim 1, wherein the predetermined signature of the authentic substance includes parameters associated with one of chemical and material composition for a given volume of the authentic substance.

12. A portable substance analysis device comprising the system of claim 1.

13. A system for determining authenticity of substances, the system comprising:
    a plurality of means for responding to an interrogation signal with a wireless unique identifier, the plurality of means for responding being arranged in a predefined location pattern relative to a location for placing the substance under analysis;
    means for transmitting sequences of interrogation signals at a plurality of power levels;
    means for receiving the wireless unique identifier of the plurality of means for responding for the sequences of the interrogation signals;
    means for housing the plurality of means for responding such that a given wireless unique identifier does not interfere with another wireless unique identifier;
    means for determining response patterns to the interrogation sequences;
    means for determining if response patterns vary outside a predetermined signature of an authentic substance; and
    means for providing an indication if the response patterns vary outside the predetermined signature of an authentic substance.

14. The system of claim 13, wherein the means for transmitting the sequences of interrogation signals comprises means for transmitting the sequences of interrogation signals over a plurality of different frequency bands at the plurality of power levels.

15. The system of claim 14, wherein the means for transmitting the sequences of interrogation signals employ spread spectrum frequency hopping to generate pseudo-random frequency bands over different sequences of interrogation signals.

16. The system of claim 13, wherein the predetermined signature of the authentic substance comprises a plurality of registered response pattern signatures associated with a known authentic substance corresponding to the substance under analysis.

17. The system of claim 13, wherein the predetermined signature of the authentic substance comprises a plurality of predetermined difference thresholds determined based on response patterns received upon obtaining a plurality of registered response pattern signatures associated with a known authentic substance corresponding to the substance under analysis.

18. The system of claim 13, wherein each response pattern is a binary sequence based on valid reads and failed reads for one or more interrogation sequences at one or more power levels.

19. A method for determining authenticity of a substance, the method comprising:
 transmitting sequences of interrogation signals in proximity of a known authentic substance over a plurality of different frequency bands at one or more power levels to a plurality of radio frequency (RF) sensors distributed in a predefined location pattern, each RF sensor being configured to respond to an interrogation signal with a unique identifier;
 registering a plurality of response pattern signatures for the known authentic substance based on first response patterns of the plurality of RF sensors to the sequence of interrogation signals;
 transmitting the sequences of interrogation signals in proximity of a substance under analysis that is purported to be the same as the known authentic substance over the plurality of different frequency bands at the one or more power levels to the plurality of RF sensors;
 analyzing second response patterns for each of the plurality of RF sensors to the sequence of interrogation signals, the second response patterns being associated with the substance under analysis; and
 transmitting a difference indicator if at least one of the second response patterns varies from a predetermined threshold associated with the plurality of registered response pattern signatures.

20. The method of claim 19, wherein registering the plurality of response pattern signatures for the known authentic substance comprises setting a plurality of the difference thresholds associated with variances of the plurality of registered response pattern signatures across the plurality of different frequency bands at the one or more power levels.

21. The method of claim 19, wherein repeatedly transmitting the sequences of interrogation signals comprises employing spread-spectrum frequency-hopping to generate pseudo-random frequency bands over different ones of the sequences of interrogation signals.

22. The method of claim 19, wherein registering the plurality of response pattern signatures for the known authentic substance comprises storing the plurality of response pattern signatures and a set of acceptable tolerances associated with each of the plurality of response pattern signatures in a database.

23. The method of claim 19, wherein analyzing the second response patterns comprises analyzing a binary sequence associated with the second response patterns that corresponds to valid reads and failed reads of the plurality of RF sensors for one or more of the sequences of interrogation signals at the one or more power levels.

* * * * *